United States Patent [19]
Fletcher et al.

[11] 3,985,454
[45] Oct. 12, 1976

[54] WINDOW DEFECT PLANAR MAPPING TECHNIQUE

[76] Inventors: James C. Fletcher, Administrator of the National Aeronautics and Space Administration, with respect to an invention of Fred R. Minton, Lakewood; Uel O. Graham, Upland, both of Calif.

[22] Filed: Mar. 14, 1975

[21] Appl. No.: 558,600

[52] U.S. Cl. ............................... 356/237; 356/239
[51] Int. Cl.² .................. G01N 21/16; G01N 21/32
[58] Field of Search ........................... 356/237, 239

[56] References Cited
UNITED STATES PATENTS

| | | | |
|---|---|---|---|
| 552,641 | 1/1896 | Hoskins | 356/239 |
| 1,514,386 | 11/1924 | Hitner | 356/239 |
| 2,871,756 | 2/1959 | Graves et al. | 356/239 |
| 3,430,055 | 2/1969 | Metzger | 356/237 |
| 3,586,444 | 6/1971 | Sproul et al. | 356/239 |
| 3,740,142 | 6/1973 | Takubo | 356/30 |

*Primary Examiner*—Vincent P. McGraw
*Attorney, Agent, or Firm*—Marvin J. Marnock; John R. Manning; Marvin F. Matthews

[57] ABSTRACT

A method of planar mapping defects in a window having an edge surface and a planar surface. The method comprises of steps of mounting the window on a support surface. Then a light sensitive paper is placed adjacent to window surface. A light source is positioned adjacent the window edge. The window is then illuminated with the source of light for a predetermined interval of time. Defects on the surface of the glass, as well as in the interior of the glass are detected by analyzing the developed light sensitive paper. The light source must be in the form of optical fibers or a light tube whose light transmitting ends are placed near the edge surface of the window.

4 Claims, 3 Drawing Figures

U.S. Patent  Oct 12, 1976  3,985,454
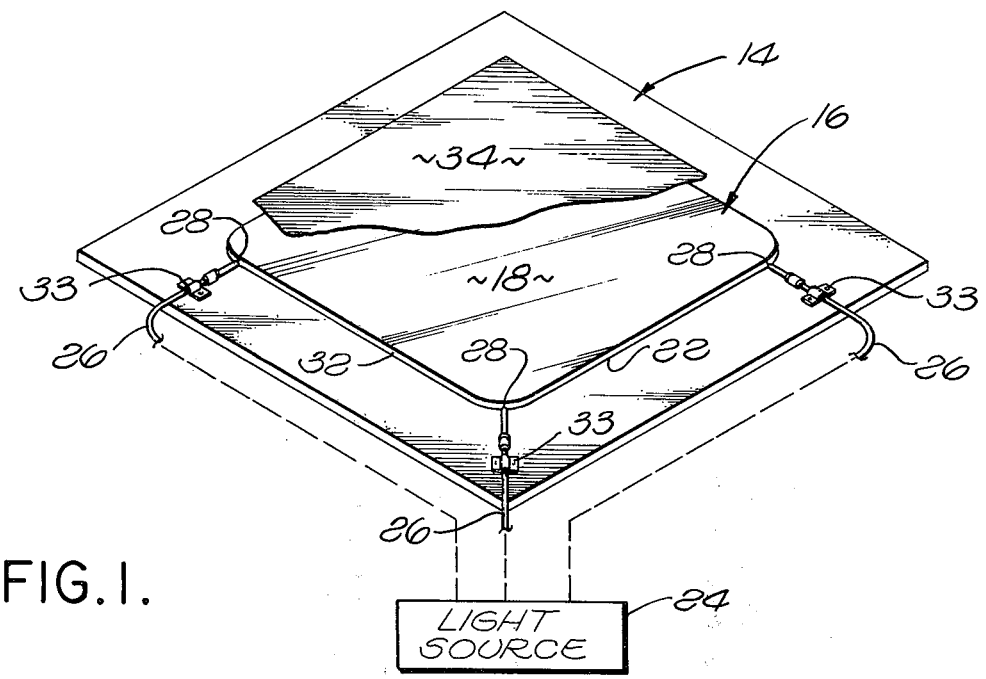
FIG.1.
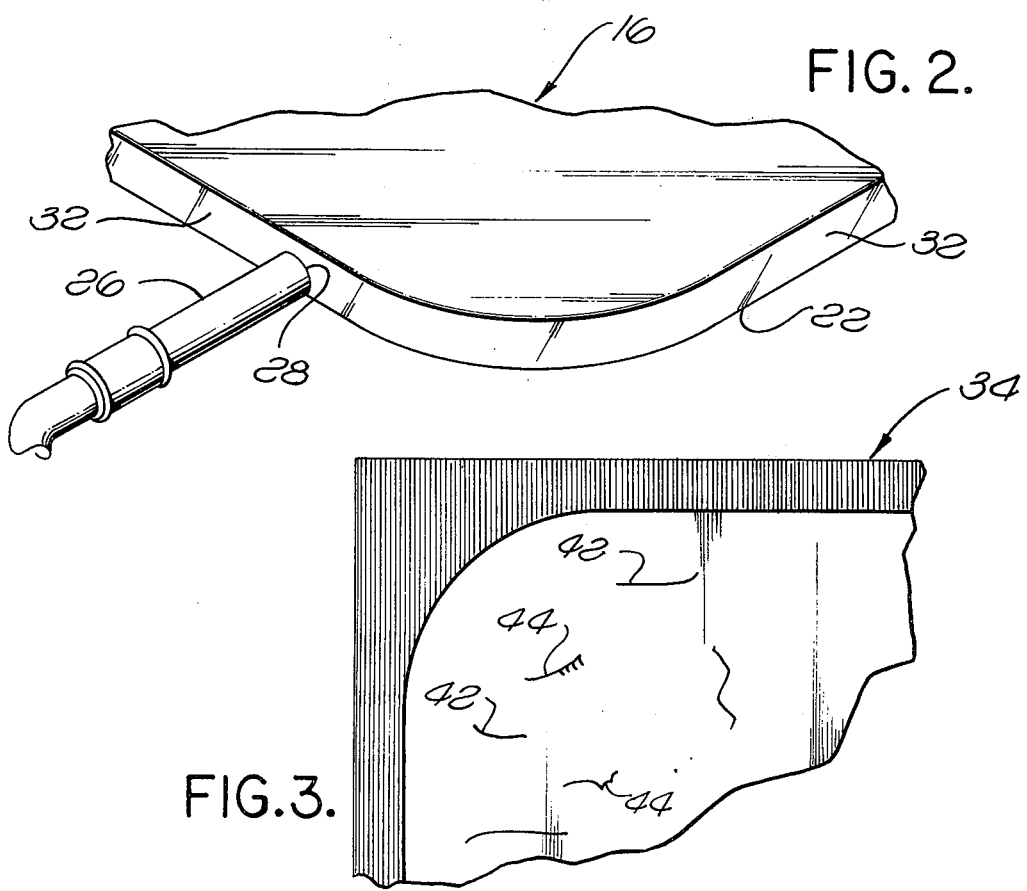
FIG.2.
FIG.3.

3,985,454

WINDOW DEFECT PLANAR MAPPING TECHNIQUE

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 45 U.S.C. 2457).

BACKGROUND OF THE INVENTION

1. Field of the Invention

The field of art to which the invention pertains includes the field of defect planar mapping techniques, particularly with respect to a method of planar mapping a transparent surface and producing a permanent record of defects therein.

2. Description of the Prior Art

Prior techniques for inspecting transparent material for flaws included directing a light source at an angle to the material surface. The light source was then swept across the entire surface and defects visually noted by the inspector. The angle of available lighting, illumination brightness, light scattering, and visual acuity of the observer combined to make the flaw detection technique extremely difficult especially where the transparent material had already been installed. Alternative techniques included the use of light measuring devices wherein a source of light was passed through the window and a light detector measured the amount of transmitted light. These systems are extremely complex and the sensitivity thereof is dependent upon the components available for transmitting and measuring the light. In addition, minute flaws on the transparent surface are normally undetectable by such techniques.

For example, in spacecraft windows, which are normally made of one-inch thick transparent material, the maximum acceptable flaw on the surface is a six ten-thousandth inch (0.0157 mm) surface defect. Should the surface defect be greater than six ten-thousandths of an inch (0.0152 mm) deep, for one-inch material, the spacecraft window is deemed unsafe for space flight where the window will be subjected to large variations in pressure between the surfaces of the window, as well as other wide variations in temperature and environmental conditions.

Known prior art includes U.S. Pat. Nos. 3,652,863; 3,639,067; 1,514,368; and 552,641.

The present invention provides a method of detecting flaws on the surface as well as the interior of a transparent material and providing a permanent record thereof. The record can then be reviewed to determine the flaws existing in the transparent material as well as their position. Once the position of the flaws have been noted, further inspection can be utilized to determine the extent or depth of the flaws.

SUMMARY OF THE INVENTION

A method of planar mapping a sheet of transparent material in order to detect defects therein. The transparent sheet is initially mounted on a support surface. Light sensitive paper is placed adjacent a planar surface of the transparent sheet of material. Transparent material is then illuminated by a source of light for a predetermined interval of time. When the light sensitive paper is developed, a permanent record is obtained of defects in the transparent material.

The advantages of this invention both as to its construction and mode of operation, will be readily appreciated as the same becomes better understood by reference to the following detailed description when considered in connection with the accompanying drawings in which like reference numerals designate like parts throughout the figures.

BRIEF DESCRIPTION OF THE DRAWINGS

FIG. 1 is a perspective view illustrating the apparatus for performing the planar mapping technique of the present invention;

FIG. 2 is a partial view, broken away, illustrating portions of the apparatus of FIG. 1, primarily the orientation of the light bundle 26 and emitting ends 28 with respect to the transparent material being examined; and FIG. 3 is a partial planar view of a developed light sensitive paper illustrating the record made of flaws in the transparent material of FIGS. 1 and 2.

DESCRIPTION OF THE PREFERRED EMBODIMENTS

Referring now to the drawings, there is shown in FIG. 1 an assembly for planar mapping a sheet of transparent material in accordance with the principles of the invention. The assembly comprises a support base 14 upon which the sheet of transparent material 16 is mounted. The first planar surface 18 of the transparent material is placed surface side up and the second planar surface 22 is positioned on the base 14.

A light source 24 provides a light output through a plurality of fibre optic guides 26. The light emitting ends 28 of the fibre optic guides are each positioned adjacent the edge 32 of the transparent material 16 so as to illuminate the transparent material as well be explained in greater detail hereinafter. A light sensitive paper 34 has its light sensitive surface positioned juxtaposed with the transparent material first planar surface 18 which is to be examined by the assembly. The fibre optic guides 26 are secured to the support base 14 by means of fasteners 33 adjacent the guide light emitting ends 28 so as to prevent movement of the guides.

When the light source 24 is activated, the sheet of transparent material 16 is illuminated by the fibre optic guide light emitting ends 28 positioned around the periphery of the transparent material. The light sensitive paper 34 is thus exposed. Subsequent conventional chemical development of the light sensitive paper 34 will provide a photographic record of defects in the transparent material 16 as will be explained in greater detail hereinafter.

For a sheet of transparent material having a length of approximately 12 inches, a width of 15 inches, and a thickness of approximately 1 inch, three one-eighth inch diameter fibre optic guides 26 whose light emitting tips 28 are placed approximately at three of the corners of the transparent material wll sufficiently illuminate the transparent material. Preferably, the transparent material contains a ground or etched edge, and the light is diffused along the transparent material perimeter and within the plane of the glass.

As illustrated in FIG. 2 the fibre optic guide 26 has its light emitting end 28 placed at the edge of the transparent material 16 so that the light from the optic guide 26 is directed into the plane of the transparent material 16. In the above specified example, a light source of approximately 35 watts output, coupled to the three fibre optic guides 26 spaced around the transparent material provides sufficient illumination of the transparent material. Utilizing Eastman Kodak Ektamatic light sensitive paper and illuminating the transparent material for 0.2 seconds provided sufficient illumination to expose the light sensitive paper sufficiently to provide excellent resolution defining all surface defects. Vacuum sealing of the contact paper to the window surface could provide even greater surface contact between the light sensitive paper and the transparent material planar surface. Alternatively, it should be understood that photographing of the illuminated transparent material could also be used to define surface defects in the transparent material. Resolution of 50 millionths of an inch (0.0013 mm) has been obtained by utilizing direct contact light sensitive paper as illustrated in FIG. 1.

However, high resolution photography is necessary in order to attain desired results. This requires expensive high resolution photographic equipment, adequate distance to get the window or item within the photo frame; time spent in developing the negative then enlarging the photograph, which requires several hours.

The planar mapping tenchique is accomplished complete, on site in a matter of seconds, with no enlargements required, resulting in an efficient, inexpensive and immediate result.

FIG. 3 illustrates an exposed and developed sheet of light sensitive paper. Lines 42 illustrate scratches on the surface of the transparent material whereas areas 44 illustrate typical coating spatters on the transparent material surface. While not illustrated, the technique can also be used to determine bubbles in the transparent material. Once the surface defects on the transparent material have been determined, conventional measuring instruments such as an optical depth micrometer can be used to measure the defect depths.

The present technique can be utilized for any transparent material, but has been primarily used with fused quartz and alumina silicate which are used as spacecraft windows and can normally accept surface scratches of six ten-thousandths of an inch where material from ¼ to 1½ inch thick is utilized.

It should further be understood that the technique could also be used to determine defects in a transparent material which has already been mounted in a spacecraft or other environment by providing ports in the adjacent mounting structure so that light could be transmitted thereto by means of fibre or rod optic guides. The guides could also be permanently secured to the structure and the light source connected to the guide terminals when needed.

We claim:
1. A method of planar mapping a sheet of transparent material having an edge surface and a planar surface, for detecting defects in the sheet of transparent material and said planar surface, said method comprising the steps of:
   a. mounting said transparent sheet on a support surface;
   b. positioning a light source adjacent the edge of said sheet of transparent material;
   c. placing a light sensitive paper adjacent said planar surface in superposed contacting relationship therewith; and
   d. illuminating said transparent material by said source of light for a predetermined interval of time thereby exposing said light sensitive paper and producing thereon a map of flaws and defects in the sheet of transparent material.
2. A method in accordance with claim 1 including the step of vacuum sealing the light sensitive paper in contacting sealed relationship with said planar surface.
3. A method in accordance with claim 1 wherein said light source energy is directed laterally through said sheet of transparent material and generally parallel to said planar surface.
4. A method in accordance with claim 1 wherein the light from said light source is transmitted by means of fibre optic guides or light tubes whose light emitting ends are spaced around the edge of the sheet of transparent material in abutting relation therewith.

* * * * *